United States Patent
Coelho et al.

[11] Patent Number: 5,975,367
[45] Date of Patent: Nov. 2, 1999

[54] FIBRIN GLUE LINE AND DOT DISPENSER

[75] Inventors: Philip H. Coelho, El Dorado Hills; Terry L. Wolf, Placerville; Pete J. Menke, Antelope; Jerry M. Alcone, Rancho Cordova, all of Calif.

[73] Assignee: ThermoGenesis Corp., Rancho Cordova, Calif.

[21] Appl. No.: 08/722,558

[22] Filed: Sep. 27, 1996

[51] Int. Cl.⁶ .................................................. B67D 5/62
[52] U.S. Cl. ........................................... 222/137; 604/82
[58] Field of Search ................... 604/82, 191; 222/137, 222/309

[56] References Cited

U.S. PATENT DOCUMENTS

| | | |
|---|---|---|
| D. 369,657 | 5/1996 | McGugan . |
| 3,269,389 | 8/1966 | Meurer et al. . |
| 4,109,653 | 8/1978 | Kozam et al. . |
| 4,359,049 | 11/1982 | Redl et al. . |
| 4,874,368 | 10/1989 | Miller et al. . |
| 4,902,281 | 2/1990 | Avoy . |
| 4,978,336 | 12/1990 | Capozzi et al. . |
| 5,104,375 | 4/1992 | Wolf et al. . |
| 5,116,315 | 5/1992 | Capozzi et al. . |
| 5,240,146 | 8/1993 | Smedley et al. . |
| 5,253,785 | 10/1993 | Haber et al. . |
| 5,271,527 | 12/1993 | Haber et al. . |
| 5,286,258 | 2/1994 | Haber et al. . |
| 5,290,259 | 3/1994 | Fischer . |
| 5,314,412 | 5/1994 | Rex . |
| 5,318,524 | 6/1994 | Morse et al. . |
| 5,322,510 | 6/1994 | Lindner et al. . |
| 5,330,079 | 7/1994 | Keller . |
| 5,330,974 | 7/1994 | Pines et al. . |
| 5,368,563 | 11/1994 | Lonneman et al. . |
| 5,378,233 | 1/1995 | Haber et al. . |
| 5,405,607 | 4/1995 | Epstein . |
| 5,423,752 | 6/1995 | Haber et al. . |
| 5,464,396 | 11/1995 | Barta et al. . |
| 5,474,540 | 12/1995 | Miller et al. . |
| 5,505,704 | 4/1996 | Pawelka et al. . |
| 5,605,541 | 2/1997 | Holm . |

*Primary Examiner*—Gregory L. Huson
*Attorney, Agent, or Firm*—Bernhard Kreten

[57] ABSTRACT

A fibrin glue dispenser including a spring biased rack. The rack spring is a coil spring having substantially linear characteristics along its operating length. The rack spring forces first and second plungers into first and second loaded syringes to dispense thrombin and fibrinogen into first and second exits such that the admixture of the two occurs for forming fibrin glue away from the exists. A dispensing lever can be controlled as to the fibrin glue formation to dispense either drops of fibrin glue or an elongate line of fibrin glue.

20 Claims, 4 Drawing Sheets

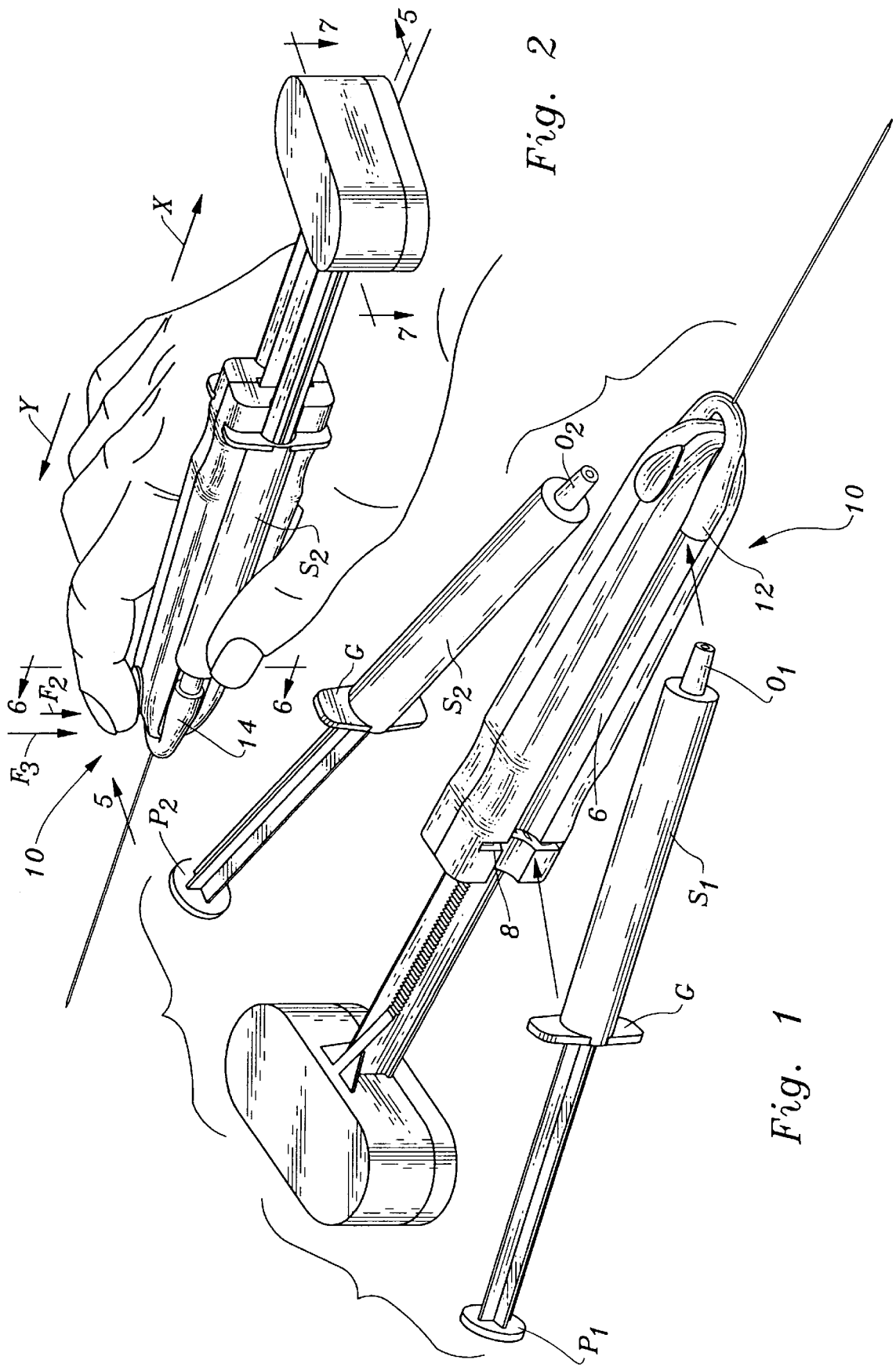

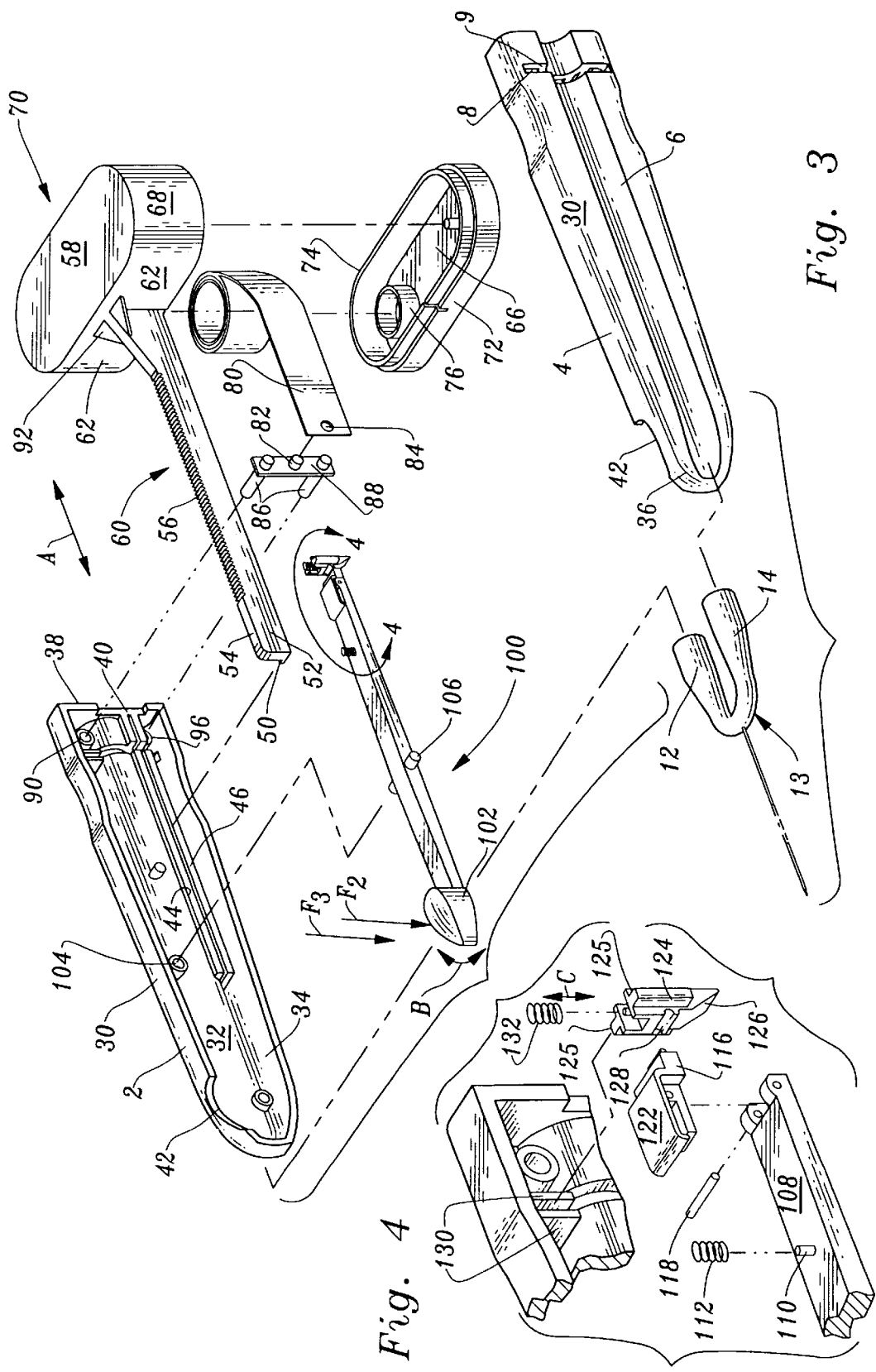

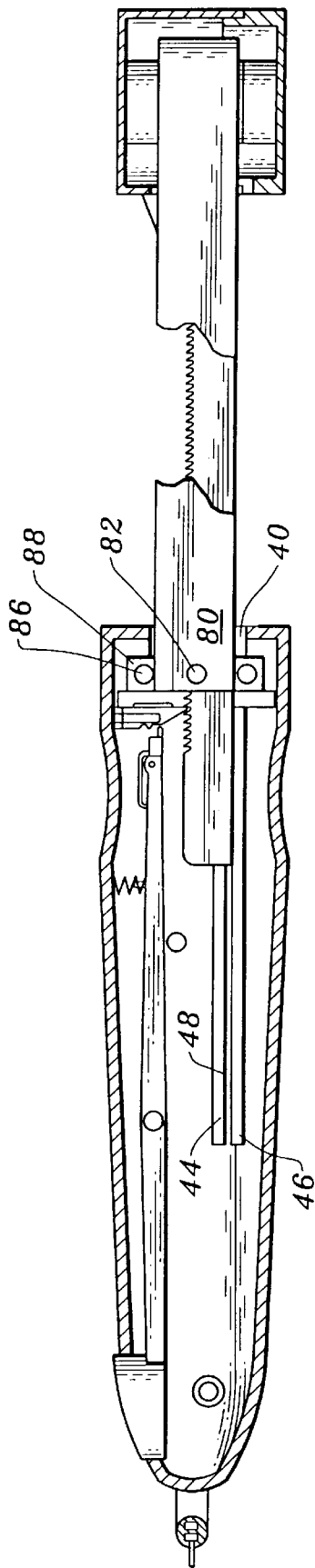
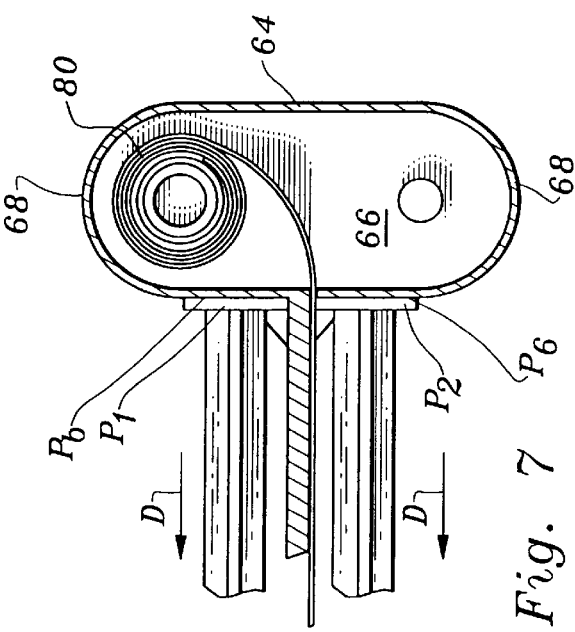
Fig. 5
Fig. 7
Fig. 6

FIBRIN GLUE LINE AND DOT DISPENSER

FIELD OF THE INVENTION

The following invention relates generally to an apparatus and method for dispensing fibrin glue either in a series of discrete drops defining dots (in which the quantum of fibrin glue is carefully controlled) or in a continuous line where the rate at which the fibrin glue is dispensed is uniform both as to cross-sectional area and rate at which the line is formed.

BACKGROUND OF THE INVENTION

Dispensers for fibrin glue should be easy to handle, non clogging, and precise in their ability to place and meter the fibrin glue at the desired site. To date, all prior art dispensers have been deficient in one or more of the above areas. Because fibrinogen, which is used to produce the fibrin glue is a relatively precious commodity, especially when the fibrinogen is derived autologously, it is imperative that the maximum efficiency possible be experienced when dispensing fibrin glue.

Precise metering has been the bane of devices which dispense fibrin glue. Metering implies that both the precise quantity of fibrin glue will be dispensed and delivered strategically to the appropriate site. Because the glue can obstruct passageways, volume variations which lead to clogging have been a recurring problem.

Impediments that exacerbate the foregoing problems include lack of an ergonomically designed dispensing tool which would facilitate usage in a natural, intuitive way. If the dispensing tool cannot be conveniently grasped, the product being delivered is less likely to be accurately deployed either to the right site or in the right amount.

Another vexing, recurring problem in mixing two component compounds involves the strategic blending of the two components at the appropriate location. A chemical process is associated with mixing the two components. Timing and location are critical. Otherwise, the chemical reaction will likely occur at an unwanted location at an unwanted time. Since fibrin glue is formed substantially immediately upon the contact of thrombin with fibrinogen, and because fibrin glue sets up almost immediately upon its formation, clogging of a dispensing tool can occur. During a surgical procedure, when fibrin glue is used to stem the flow of blood, malfunctions of a fibrin glue delivering tool can have adverse consequences. One corollary to the problem of clogging involves the fact that the thrombin and fibrinogen are typically loaded into the dispensing device with syringes. Should a clog occur, either the dispensing instrumentality has to be cleaned or replaced under aseptic conditions since the fibrinogen and thrombin earmarked for that procedure should be salvaged if at all possible.

The following prior art reflects the state of the art of which applicant is aware and is included herewith to discharge applicant's acknowledged duty to disclose relevant prior art. It is stipulated, however, that none of these citations teach singly nor render obvious when considered in any conceivable combination the nexus of the instant invention as especially claimed and as set forth in greater detail hereinafter.

| PATENT NO. | ISSUE DATE | INVENTOR |
|---|---|---|
| 4,874,368 | October 17, 1989 | Miller, et al. |
| 5,104,375 | April 14, 1992 | Wolf, et al. |

-continued

| PATENT NO. | ISSUE DATE | INVENTOR |
|---|---|---|
| 5,116,315 | May 26, 1992 | Capozzi, et al. |
| 5,240,146 | August 31, 1993 | Smedley, et al. |
| 5,253,785 | October 19, 1993 | Haber, et al. |
| 5,271,527 | December 21, 1993 | Haber, et al. |
| 5,286,258 | February 15, 1994 | Haber, et al. |
| 5,290,259 | March 1, 1994 | Fischer |
| 5,314,412 | May 24, 1994 | Rex |
| 5,318,524 | June 7, 1994 | Morse, et al. |
| 5,322,510 | June 7, 1994 | Lindner, et al. |
| 5,330,079 | July 19, 1994 | Keller |
| 5,330,974 | July 19, 1994 | Pines, et al. |
| 5,368,563 | November 29, 1994 | Looneman, et al. |
| 5,378,233 | January 3, 1995 | Haber, et al. |
| 5,405,607 | April 11, 1995 | Epstein |
| 5,423,752 | June 13, 1995 | Haber, et al. |
| 5,464,396 | November 7, 1995 | Barta, et al. |
| 5,474,540 | December 12, 1995 | Miller, et al. |
| 5,505,704 | April 9, 1996 | Pawelka, et al. |

SUMMARY OF THE INVENTION

The instant invention is distinguished over the known prior art in a multiplicity of ways.

One hallmark of the instant invention is the ergonomically kind manner in which the dispensing tool can be addressed for utilization. The contour of the instant invention is an elongate cylinder, and therefore lends itself to being grasped in the same way as a writing instrument. In addition, the device is balanced in one's hand such that the weight is well distributed fore and aft of the user's fulcrum area which occurs at the bight portion between the fore finger and the thumb of a user.

Dispensing the fibrin glue entails providing pressure using one's index finger against a dispensing button located adjacent a discharge end of the tool. The button operatively communicates with a dispensing lever that includes two forms of tactile feedback in the form of non-linear spring pressure so that the user can readily distinguish between a first light resistance (allowing the user to dispense an elongate ribbon of fibrin glue that is dispensed uniformly both as to rate and volume) or with the application of a second heavier finger pressure (allowing the dispensation of a known amount of fibrin glue in the form of a drop).

Nozzle geometry (which mixes the two components forming the fibrin glue, namely thrombin and fibrinogen) makes the likelihood of nozzle clogging particularly remote. A thrombin outlet, disposed centrally is surrounded by an annular fibrinogen dispenser whose outlet is removed slightly away from the thrombin outlet so that the thrombin outlet leads the fibrinogen outlet by an appreciable distance. In this manner, the fibrinogen and thrombin are allowed to mix, set and form fibrin glue only on the site to be glued and not at the nozzle, thereby preventing the nozzle from becoming clogged.

OBJECTS OF THE INVENTION

Accordingly, it is a primary object of the present invention to provide a new and novel fibrin glue dispensing tool.

A further object of the present invention is to provide a device as characterized above which allows a known quantity of fibrin glue to be dispensed uniformly and at a fixed rate, either as a line and/or as one or more drops.

A further object of the present invention is to provide a device as characterized above in which the dispenser can be handled by the user in a ergonomically beneficial manner to ensure both accurate dispensation of the fibrin glue and to minimize operator fatigue.

A further object of the present invention is to provide a device as characterized above which lends itself to mass production techniques and therefore may be disposable.

A further object of the present invention is to provide a device as characterized above which provides first and second feedback actuation pressures to the operator so that a dear line of demarcation exists between the dispensing of a line of fibrin glue or a drop.

A further object of the present invention is to provide a device as characterized above which is less likely to become clogged.

Viewed from a first vantage point, it is an object of the present invention to provide a device for dispensing fibrin glue comprising a support means for receiving a first syringe of thrombin and a second syringe of fibrinogen, a device which engages plungers of the syringes, means for urging the plungers from an extended position to a retracted position where the plungers will have pushed the contents of the syringes out, and means for controlling the rate at which the contents of the syringes are dispensed.

Viewed from a second vantage point, it is an object of the present invention to provide a dispenser for fibrin glue in which a removable nozzle means is operatively coupled to a dispenser body and in which said nozzle means includes first and second passageways for receiving thrombin in a first passageway having a first outlet and fibrinogen in a second passageway having a second outlet, where said first outlet for said thrombin is centrally disposed compared to said second outlet for fibrinogen which is concentrically oriented with respect to said thrombin outlet and spaced therefrom to preclude migration therebetween.

Viewed from a third vantage point, it is an object of the present invention to provide a method for dispensing fibrin glue, the steps including loading thrombin into a first syringe, loading fibrinogen into a second syringe, orienting each syringe to a dispenser such that extended plungers of said thrombin syringe and fibrinogen syringe operate in concert, and operating a push button in one of three positions including means to dispense the fibrin glue either in a ribbon, a drop or not at all.

These and other objects will be made manifest when considering the following detailed specification when taken in conjunction with the appended drawing figures.

BRIEF DESCRIPTION OF THE DRAWINGS

FIG. 1 is perspective view of the apparatus according to the present invention about to be armed with a first syringe containing thrombin and a second syringe containing fibrinogen.

FIG. 2 is a perspective view of the armed device being ergonomically grasped by a user.

FIG. 3 is an exploded parts perspective view of the apparatus according to the present invention.

FIG. 4 is a detailed view of a stop mechanism and release mechanism according to the present invention.

FIG. 5 is a sectional view taken along lines 5—5 of FIG. 2 showing both the stop and release mechanism and its coaction with a rack.

FIG. 6 is a sectional view taken along lines 6—6 of FIG. 2.

FIG. 7 is a sectional view taken along lines 7—7 of FIG. 2.

DESCRIPTION OF PREFERRED EMBODIMENTS

Figure 8:
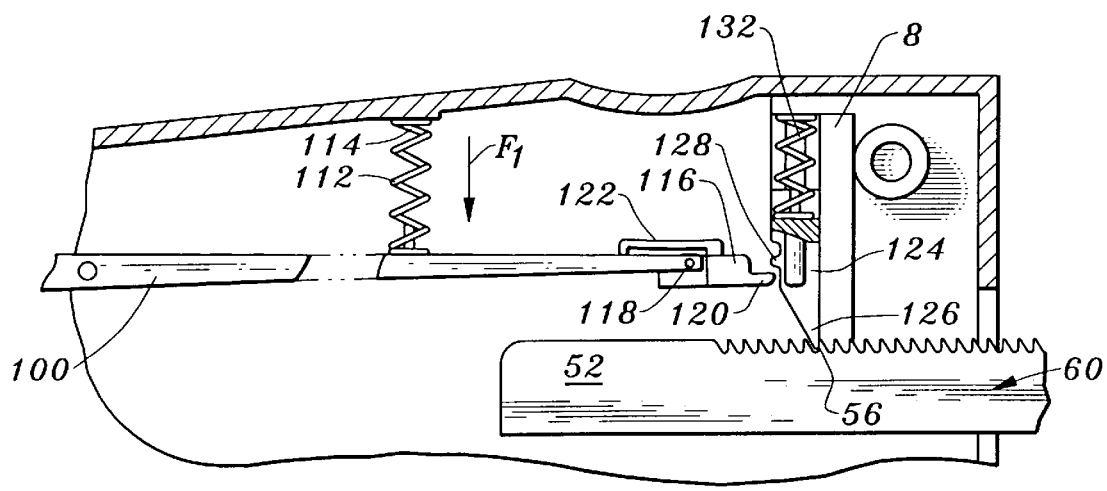
FIG. 8 details the dispensing lever according to the present invention schematically showing the stop mechanism and its coaction with the rack.

Referring to the drawings, wherein like reference numerals denote like parts throughout the various drawing figures, reference numeral 10 is directed to the dispenser according to the present invention.

In its essence, the dispenser 10 can be handled in much the same manner a pen or pencil is grasped by a user (FIG. 2). The dispenser 10 includes means on opposite sides thereof for accommodating a first syringe S1 containing thrombin therewithin and a second syringe S2 containing fibrinogen. Each syringe has a respective plunger, P1, P2 adapted to reciprocate within an interior hollow of the syringe and each syringe has an outlet O1, O2 respectively for dispensing its contents after it has docked with an outlet receiving portal 12, 14, one for each outlet. The portals 12, 14 are located on the dispenser 10. The plunger P is engaged along a back wall thereof by a spring biased housing 70 that urges a rack assembly 60 to reciprocate from a first extended position (FIG. 2), substantially coextensive with the plunger when it is fully loaded and retracted from the hollow of the syringe to a second contracted position where the plunger is nested totally within the hollow of the syringe, defining an empty syringe.

More particularly, and with respect to FIG. 3, the dispenser 10 includes a first housing portion 2 and a second housing portion 4. The housings 2, 4 are substantially mirror images of the other with the exception of male and female frictional fastenings to unite the two halves of the housing together.

The housings are divided along a vertical plane substantially at a mid-point of the device. Each housing has an arcuate channel way 6 on an outer lateral face thereof, the arcuate channel way having a radius of curvature comparable to the outside curvature the syringes S1, S2 so that the syringes can nest therewithin. In addition, the housings 2, 4 include a slit 8 passing through the housings and located strategically adjacent a "finger grip" portion G of the syringe where traditionally the index finger and middle finger of the hand grasp the syringe. A retention bump 9 or bumps appear in the slit 8 to enhance retaining the syringe.

In common use, the syringes are operated by placing the thumb on the plunger at a distal extremity remote from the syringe body and grasping the syringe along the area G so that the motion of pushing the thumb close to the fore finger and middle finger of the hand drives the plunger into the hollow of the syringe. Prior art fibrin glue dispensers mimic this motion which is ergonomically imprecise.

In the present case, by contrast, the finger purchase area G is received within the slit 8 disposed on each housing. The outlets O1, O2, of the syringe each communicate with a manifold 13 having portal inlet 12 which receives outlet O1, of syringe S1 and portal inlet 14 which receives outlet O2 of syringe S2. FIG. 6 shows the detail of that frictional fit.

Therein, conical walls of the portal inlets 12 and 14 have outwardly diverging tapers complemental to the luer contour of the outlets O1 and O2. Thus, the syringes are loaded by first placing the outlet O into the portal and then the finger purchase area G of the syringe in the slit 8 so that the syringe body S can nest within the arcuate portion 6 of the housing of the dispenser 10. The plunger P has a back face Pb which rests upon a front wall 62 of the spring biased housing 70 so that, as the housing 70 advances towards the dispenser housing 2, 4, as will be explained, the plungers are pressed into the hollows of the syringes.

Referring again to FIG. 6, the first portal 12 communicates with a passageway 22 that leads to an annular passageway 24 and then to annular conduit 26 and thence to exit 27. Preferably, fibrinogen is dispensed from this conduit 26. Preferably, elements 16, 18, 22, 24, 26 and 28 have small dimensions to minimize ullage. Thrombin, contained in syringe S2 passes through a similar passageway 16 and into a central chamber 18 and thereafter through a central passageway 28 to an exit 29. Notice that the exit 29 of the central passageway 28 is removed from the exit 27 by a distance d. This increases the likelihood that one compound will be dispensed in advance of the other when using the dispenser 10 so that the thrombin will not come into contact with the fibrinogen especially near the fibrinogen exit. This would cause clogging of the fibrinogen exit. Note, however, that even should dogging occur, the manifold 13 and portals 12, 14 can be easily replaced since they are also frictionally held within the arcuate trackway 6 on the housing.

The preceding description implies that when loaded as just described (fibrinogen in portal 12), the dispenser 10 is best "pulled" in use (i.e. direction X of FIG. 2). If the syringes were reversed (i.e. thrombin in portal 12), the dispenser should be "pushed" (i.e. direction Y of FIG. 2). This helps prevent exit clogging because the thrombin is the more "active" (responsible) for exit clogging and it is therefore best to sequester the thrombin from the fibrinogen exit.

The housings 2 and 4 (FIG. 3) each include a top wall 30, a side wall 32 and a bottom wall 34. A front wall 36 (nose) has an arcuate slope leading down to the bottom wall 34. A back wall 38 includes clearance 40 for the rack assembly 60 and coil spring 80 to be described. The sloped front wall 36 of each housing includes an arcuate cutaway 42 near the top wall to receive a dispensing button 102 to be described. The interior wall 32 of the housing half 2 includes a trackway 44, 46 with the top part of the track 44 parallel and spaced from the bottom part of the track 46 by a gap 48 substantially the dimension of a shelf 50 that extends from a lower lateral side of the rack 60. This shelf 50 serves as a slide providing support for the rack 60 as it moves from a first extreme position (e.g. FIG. 2) to a contracted position within the dispenser housing 2, 4. The trackway 44, 46, 48 is somewhat parallel to the top wall 30 and bottom wall 34.

The rack 60 includes a vertical wall 52 extending up from the shelf 50. A top surface 54 of the rack 60 includes a plurality of rack teeth 56 extending substantially along the entire medial extent thereof. The rack 60 terminates in a top portion of the spring biased housing 70. The top portion includes a top wall 58, a front wall 62 against which the ends of the plungers P1, P2 abut, a back wall 64 and two arcuate end walls 68 which connect the front wall 62 and the back wall 64.

A bottom portion of housing 70 includes a bottom wall 66 which is separable from the top wall by means of an upwardly extending peripheral lip 72 which has an inwardly oriented offset leading to an upwardly extending ledge 74. The walls 62, 64, 68 frictionally nest over the ledge 74 and abut against lip 72.

The floor 66 includes a spool 76 over which one end of the coil spring 80 is fixed and multiple turns are supported. The coil spring provides substantially linear resistance over its length and pays out as the rack 60 moves from a proximate position to the back wall 38 to a remote position along the double ended arrow "A" of FIG. 3.

The spring 80 is constrained to operate under tension by means of the spring 80 having been affixed to the housing 2 via a support pin 82 which passes through a hole 84 on a free end of the spring 80. Two pegs 86 interconnected by a web 88 support the pin 82 and pegs 86 and are received in corresponding orifices 90 on the housing half 2. A gusset 92 at an end of the rack 60 adjacent the spring housing 70 provides further support from flexing and facilitates the device being operated with only one syringe should it be desired.

As has been described so far, upon loading the syringes into the dispenser 10 and moving the rack to the FIG. 2 extended position and placing the syringes as above described, release of the spring 80 would cause all of the contents within the syringes to be paid out immediately. However, a dispensing lever 100, including a stop and release Referring to FIGS. 3, 4, 5 and 8 through 11, the operation of the dispensing lever can be explored. As shown in FIG. 3, a dispensing lever 100 has a first end with a push button 102 that protrudes within the cutaways 42 on the housing halves 2, 4. The push button 102 allows arcuate motion of the dispensing lever 100 along the direction of the double ended arrow "B" by virtue of its pivotal connection to interior bores 104 on the housing via lever pivot 106. Motion of the button downwardly ($F_2$) causes a corresponding rise in an opposite end of the dispensing lever 100 and in a direction $F_2$.

The end of the dispensing lever 100 remote from the push button 102 is best seen in FIGS. 4 and 8. The lever 100 includes a top surface 108 upon which a spring support 110 is disposed. A non-linear spring 112 is captured between the spring support 110 and a pip 114 (FIG. 8) located on an underside of the top wall 30. This spring tends to exert a force $F_1$ encouraging the lever arm 100 to remain in an at rest, FIG. 1 position. A free end of the lever 100 remote from the push button 102 includes a dog 116 connected to a free end of the lever 100 by means of a pivot 118. The dog 116 has a projection 120. A top surface bridging between the dog 116 and a portion of the lever near the pivot 118 includes an overlying break spring 122 in the form of a leaf-type spring which encourages the dog 116 to remain in the at rest position shown in FIG. 8.

FIGS. 4 and 8 also reflect a slide 124 having a tooth 126 at a lowermost extremity. In addition, the slide includes a boss 128 located proximate to the projection 120. The slide 124 is sandwiched between two tangs 130 depending from an underside of the top wall 30 of the housings 2, 4. Shoulders 125 on the slide constrain the slide to pure vertical motion in the direction of the double ended arrow "C". A spring 132 encourages the slide to be in an at rest position shown in FIG. 8 in which the tooth 126 resides between two teeth 56 on the rack 60.

Figure 9:
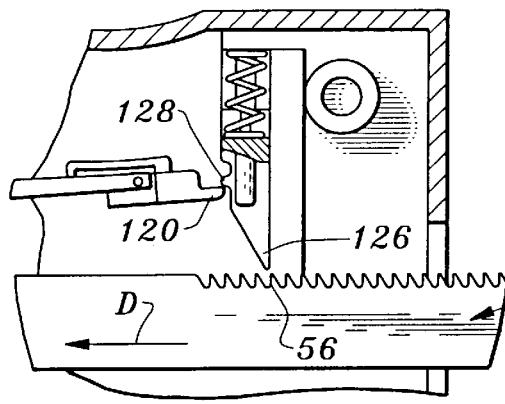
FIG. 9 shows the release and stop mechanism of the dispensing lever allowing a ribbon of material to be dispensed.

Assume that the user of FIG. 2 exerts a force $F_2$ on the button 102. Assume further that the quantum of force is such that the projection 120 of FIG. 9 is sufficient only to overcome a certain amount of the spring tension in spring 112 and in spring 132 so that the boss 128 remains in contact above the projection 120. Notice that the tooth 126 is now spaced from the teeth 56 on the rack 60 and the rack 60 therefore is allowed to have the spring 80 coil wind onto its spool 76. Retraction of the spring into the housing causes the rack to move in the direction of the arrow "D" of FIG. 9. This causes concomitant motion of the plungers P1 and P2 also in the direction "D" allowing the contents of the syringes to be paid out through the exits 27, 29 for so long as the protuberance 120 supports the boss 128. Removal of the force $F_2$ causes the dog 116 to go back to its FIG. 8 position and the tooth 126 is caught in the teeth 56 preventing any further dispensing.

Figure 10:
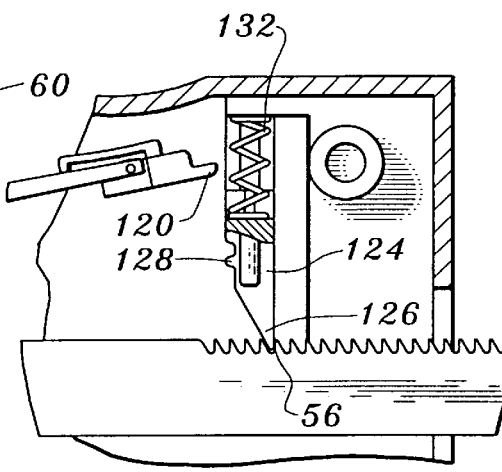
FIG. 10 shows a situation in which a drop is to have been dispensed.
Figure 11:
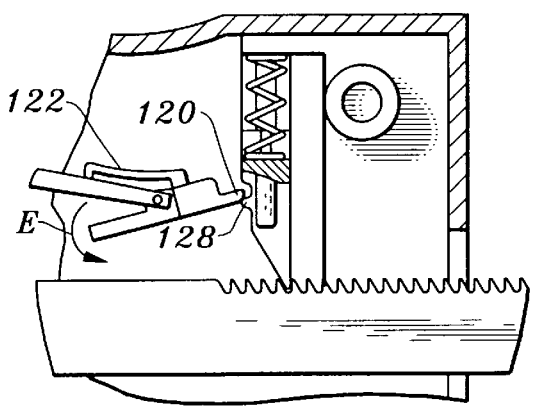
FIG. 11 shows reinitialization from the FIG. 10 position back to the FIG. 8 position after a drop has been dispensed.

In FIG. 10 a greater force $F_3$ is applied and the protuberance 120 is now on a top side of the boss 128. Spring 132 forces tooth 126 quickly back into rack teeth 56, dispensing only a "drop" of thrombin and fibrinogen. Next, after removal of the force $F_3$, the force of the spring 112 (FIG. 8) is great enough (FIG. 11) to cause the dog 116 to go back down and pivot the dog about the arrow "E". This pivoting is opposed slightly by the break spring 122. However, once the protuberance 120 is beyond the boss 128, the FIG. 8 configuration will have been arrived at.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. A device for dispensing fibrin glue comprising, in combination:
    a support means for receiving a first syringe body containing thrombin and a second syringe body containing fibrinogen,
    a holder which engages plungers of the syringes,
    urging means coupling said support means and said holder for pushing the plungers from an extended position to a retracted position where the plungers will have pushed out the contents of the syringes, and
    means for controlling the rate at which the contents of the syringes are dispensed integrated in said support means, said urging means and said holder.

2. A dispenser for fibrin glue formed from first and second fibrin glue components in which a removable nozzle means is operatively coupled to a dispenser body and in which said nozzle means includes first and second passageways for receiving the first fibrin glue component in said first passageway having a first outlet and the second fibrin glue component in said second passageway having a second outlet, and
    said first passageway centrally located, said second passageway is concentrically oriented with respect to said first passageway.

3. A method for dispensing fibrin glue, the steps including:
    loading thrombin into a first syringe while extending the syringe's plunger,
    loading fibrinogen into a second syringe while extending the syringe's plunger,
    orienting each syringe to a dispenser such that extended plungers of said thrombin syringe and fibrinogen syringe operate in concert,
    tensioning both plungers so that the plungers are urged to simultaneously dispense the syringe's contents, and
    operating a push button and coupling the button to a tensioning release to allow one of three release profiles including dispensing the fibrin glue either in a ribbon, a drop or not at all.

4. A dispenser for fibrin glue in which a removable nozzle means is operatively coupled to a dispenser body and in which said nozzle means includes a first passageway having a first outlet and a second passageway having a second outlet, and
    said first passageway having a greater length compared to said second passageway such that said first outlet is axially spaced from said second outlet.

5. The device of claim 1 wherein said urging means includes biasing means extending between said support means and said holder and said means for controlling the rate at which the contents of the syringes are dispensed includes a release for said biasing means.

6. The device of claim 5 wherein said release includes force responsive means which in the presence of no force holds said urging means in fixed position, and the presence of a first force allows said biasing means to dispense a continuous stream from said syringes and a third position responsive to a third force magnitude which interrupts dispensing from said syringes.

7. The device of claim 6 including anti-fouling means adjacent syringe outlets.

8. The device of claim 7 wherein said anti-fouling means includes a pair of axially aligned passageways, each having outlets, one outlet terminating along its longitudinal extent at a locale different from another said outlet.

9. The device of claim 8 wherein said passageways are concentrically oriented.

10. The device of claim 9 wherein support means are formed from a first and second housing interconnected to define a hollow interior, said housings are substantially mirror images of each other and frictionally connected together by complemental male and female frictional fastenings.

11. The device of claim 10 wherein said housings include an access slit on each said housing exposing a button which when engaged releases said biasing means and allows plunger advancement.

12. The device of claim 11 wherein said button is operatively coupled to a lever which selectively releases and engages said biasing means.

13. The dispenser of claim 2 wherein said first passageway and said second passageway outlets are spaced one from the other to preclude and prevent contact of said first fibrin glue component with said second fibrin glue component at one of said outlets when said dispenser is moved linearly.

14. The dispenser of claim 13 wherein said dispenser includes biasing means operatively coupled thereto to push the first fibrin component and the second fibrin component through said passageways.

15. The dispenser of claim 14 including means for stopping the flow of the first fibrin component and the second fibrin component through said passageways.

16. The method of claim 3 the steps further including dispensing from one syringe at a locale different from dispensing from the other syringe to preclude the contents of one syringe from reacting with the contents of the other syringe when drawing the contents out from the syringes.

17. The dispenser according to claim 4 in which said dispenser body includes means to support a body portion of a syringe thereon and moveable plunger support means operatively coupled to said dispenser body having biasing means interposed therebetween to force the plunger into the syringe body.

18. The dispenser of claim 17 including stop means integrally formed in said dispenser body which arrests advancement of the plunger into the body of the syringe.

19. The dispenser of claim 18 in which the dispenser includes a push button which operates said means for arresting the plunger.

20. The dispenser of claim 19 wherein said first passageway is concentric to said second passageway.

* * * * *